US006166073A

United States Patent [19]
Dean et al.

[11] Patent Number: 6,166,073
[45] Date of Patent: Dec. 26, 2000

[54] COMBINATIONS OF DP AND FP TYPE PROSTAGLANDINS FOR LOWERING IOP

[75] Inventors: Thomas R. Dean, Weatherford; Mark Hellberg, Arlington; Verney L. Sallee, Southlake, all of Tex.

[73] Assignee: Alcon Laboratories, Inc., Fort Worth, Tex.

[21] Appl. No.: 09/365,454

[22] Filed: Aug. 2, 1999

Related U.S. Application Data

[63] Continuation of application No. 09/033,282, Mar. 2, 1998, abandoned, which is a continuation of application No. 08/577,039, Dec. 22, 1995, abandoned.

[51] Int. Cl.$^7$ .......................... A61K 31/215; A61K 31/19
[52] U.S. Cl. ......................... 514/530; 514/573; 514/913
[58] Field of Search ...................................... 514/530, 573, 514/913

[56] References Cited

U.S. PATENT DOCUMENTS

| | | |
|---|---|---|
| 4,029,681 | 6/1977 | Smith . |
| 4,097,489 | 6/1978 | Bundy . |
| 4,288,616 | 9/1981 | Sih . |
| 4,599,353 | 7/1986 | Bito . |
| 5,173,507 | 12/1992 | DeSantis et al. . |
| 5,296,504 | 3/1994 | Stjernschantz et al. . |
| 5,321,128 | 6/1994 | Stjernschantz et al. . |
| 5,565,492 | 10/1996 | DeSantis et al. . |

FOREIGN PATENT DOCUMENTS

| | | |
|---|---|---|
| 0 289 349 A1 | 11/1988 | European Pat. Off. . |
| 0 299 914 A1 | 1/1989 | European Pat. Off. . |
| 0 308 135 A2 | 3/1989 | European Pat. Off. . |
| 0 458 642 A1 | 11/1991 | European Pat. Off. . |
| 0 569 046 A1 | 11/1993 | European Pat. Off. . |
| 0 364 417 B1 | 2/1994 | European Pat. Off. . |
| 0 603 800 A1 | 6/1994 | European Pat. Off. . |
| 0 639 563 A2 | 2/1995 | European Pat. Off. . |
| WO 90/02553 | 3/1990 | WIPO . |
| WO 94/05631 | 3/1994 | WIPO . |

OTHER PUBLICATIONS

Alm, Effects of Topically Applied PGF$_{2\alpha}$ and Its Isopropylester On Normal and Glaucomatous Human Eyes, *Progress in Clinical Biological Research*, Alan R. Liss, Inc., pp. 447–458 (1989).

Alm, The potential of prostaglandin derivates in glaucoma therapy, *Current Opinion in Ophthalmology*, vol. 4, No. 11, pp. 44–50 (1993).

Barraclough, Synthesis and Platelet Aggregation Inhibiting Activity of Acid Side–chain Modified Hydantoin Prostaglandin Analogues, *Archives in Pharmacology*, vol. 326, No. 2, pp. 85–95 (1993).

Brubaker, Fluorophotometric Studies of Prostaglandin Effects On the Human Eye: The Lack of Association of Reduced Intraocular Pressure with Altered Flow of Barrier Function, *Progress in Clinical and Biological Research*, vol. 393, Alan R. Liss, Inc., pp. 477–481 (1989).

Bundy, Synthesis and Platelet Aggregation Inhibiting Activity of Prostaglandin D Analogues, *Journal of Medicinal Chemistry*, vol. 26, pp. 790–799 (1983).

Crawford, Effects of topical PGF$_{2\alpha}$ on aqueous humor dynamics in cynomolgus monkeys, *Current Eye Research*, vol. 6, No. 8, pp. 1035–1044 (1987).

Das, 9,11–Epoxy–9–homoprosta–5–enoic Acid Analogues as Thromboxane A$_2$ Receptor Antagonists, *Journal of Medicinal Chemistry*, vol. 33, No. 6, pp. 1741–1748 (1990).

Giles et al., A comparative study of the prostanoid receptor of 9$\alpha$11$\beta$–prostaglandin F$_2$ and prostaglandin D$_2$, *British Journal Pharmacol.*, vol. 104, pp. 541–549 (1991).

Giuffre, The Effects of Prostaglandin F$_{2\alpha}$ the Human Eye, *Graefe's Archieve Ophthalmology*, vol. 222, pp. 139–141 (1985).

Goh, Effect of topical prostaglandin D$_2$ on the aqueous humor dynamics in rabbits, *Graefe's Archive Clin. Exp. Ophthalmology*, vol. 227, pp. 476–481 (1989).

Goh, Effects of Prostaglandin D$_2$ and Its Analogues on Intraocular Pressure in Rabbits, *Jpn J. Opthalmol.*, vol. 32, pp. 471–480 (1988).

Kerstetter, Prostaglandin F$_{2\alpha}$–1–Isopropylester Lowers Intraocular Pressure Without Decreasing Aqueous Humor Flow, *American Journal of Opthalmology*, vol. 105, pp. 30–34 (1988).

Krauss et al., Prostanoid FP–receptor mediated contractions of the cat iris sphincter depend on calcium influx, *FASEB J*, vol. 5, No. 4, p. A476 (1991), abstract 609.

Lake, Cloning of the rat and human prostaglandin F$_{2\alpha}$ receptors and the expression of the rat prostaglindin F$_{2\alpha}$ receptor, *FEBS Letters 355*, pp. 317–325 (1994).

Nakajima, Effects of Prostaglandin D$_2$ and its analogue, BW245C, on Intraocular Pressure in Humans, *Graefe's Archive Opthalmology*, vol. 229, pp. 411–413 (1991).

Sharif, N.A., Williams, G.W. and DeSantis, L.M. *Neurochemistry Research*, vol. 20, pp. 669–674 (1994).

Sharif, N.A., Xu, S. and Yanni, J.M. *Journal of Ocular Pharmacology*, vol. 10, pp. 653–664 (1994).

Thierauch, Prostaglandins and their Receptors: II. Receptor Structure and Signal Transduction, *Journal of Hypertension*, vol. 12, pp. 1–5 (1994).

UF–021, *Drugs of the Future*, 17(3), pp. 193–196 (1992).

Veldhuis, Prostaglandin F$_{2\alpha}$Initiates Polyphosphatidylinositol Hydrolysis and Membrane Translocation of Protein Kinase C In Swine Ovarian Cells, *Biochemical and Biophysical Research Communications*, vol. 149, No. 1, pp. 112–117 (1987).

Woodward, Ca$^{2+}$ Transients Evoked By Prostanoids in Swiss 3T3 Cells Suggest an FP–Receptor Mediated Response, *Advances in Prostaglandin, Thromboxane, and Leukotriene Research*, vol. 21, edited by B. Sameulsson et al., Raven Press, Ltd., New York, pp. 367–370 (1990).

*Primary Examiner*—Zohreh Fay
*Attorney, Agent, or Firm*—Michael C. Mayo

[57] ABSTRACT

Compositions containing DP-agonist and FP-agonists prostaglandin agonists and methods of their use in treating glaucoma or ocular hypertension are disclosed.

16 Claims, No Drawings

COMBINATIONS OF DP AND FP TYPE PROSTAGLANDINS FOR LOWERING IOP

This application is a continuation of U.S. patent application Ser. No. 09/033,282, filed Mar. 2, 1998 now abandoned; which is a continuation of U.S. patent application Ser. No. 08/577,039, filed Dec. 22, 1995. Now abandoned.

The present invention relates to the treatment of glaucoma and ocular hypertension. In particular, the present invention relates to the use of combinations of prostaglandin D-series and prostaglandin F-series compounds to treat glaucoma and hypertension.

BACKGROUND OF THE INVENTION

Glaucoma is a progressive disease which leads to optic nerve damage, and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The reasons why aqueous humor accumulates are not fully understood. It is known that the elevated intraocular pressure ("IOP") can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics.

All types of drugs currently being used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis which can affect patient compliance and/or necessitate the withdrawal of treatment. Moreover, some beta-blockers have increasingly become associated with serious pulmonary side effects attributable to their effects on beta-2 receptors in pulmonary tissue. Sympathomimetics cause tachycardia, arrhythmia and hypertension. There is therefore a continuing need for therapies which control the elevated intraocular pressure associated with glaucoma.

Prostaglandins, which are metabolite derivatives of arachidonic acid, have recently been pursued for possible efficacy in lowering IOP. The arachidonic acid cascade is initiated by the conversion of arachidonic acid to prostaglandin $G_2$ and subsequent conversion to prostaglandin $H_2$. Other naturally occurring prostaglandins are derivatives of prostaglandin A number of different types of prostaglandins have been discovered including A, B, D, E, F and I-Series prostaglandins. Of interest in the present invention are combinations of compounds which exhibit similar IOP lowering mechanisms as $PGD_2$, formula (I) and $PGF_{2\alpha}$, formula (II):

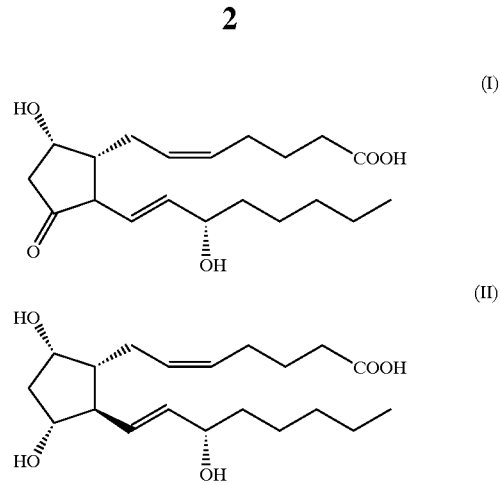

The relationship between $PGD_2$ receptor activation and IOP lowering effects is not well known. Various publications have reported that $PGD_2$ receptor activation leads to second messenger activation and in particular, to the stimulation of adenylate cyclase and resultant increases in cAMP levels (Thierauch, *Prostaglandins and their Receptors: II. Receptor Structure and Signal Transduction, Journal of Hypertension,* volume 12, pages 1–5 (1994). Regardless of mechanism, $PGD_2$ has been shown to lower IOP (Nakajima, *Effects of Prostaglandin $D_2$ and its analogue, BW245C, on Intraocular Pressure in Humans, Graefe's Archive Ophthalmology,* volume 229, pages 411–413 (1991)). Thus, it has been of interest in the field to develop synthetic $PGD_2$ analogues with IOP lowering efficacy.

Synthetic $PGD_2$-type analogs have been pursued in the art (*Graefe's Archive Ophthalmology,* volume 229, pages 411–413 (1991)). Though $PGD_2$-type molecules lower IOP, these types of molecules have also been associated with undesirable side effects resulting from topical ophthalmic dosing. Such effects have included an initial increase in IOP, conjuctival hyperemia, increases in microvascular permeability, and increases in eosinophile infiltration (Alm, *The Potential of Prostaglandin Derivatives in Glaucoma Therapy, Current Opinion in Ophthalmology,* volume 4, No. 11, pages 44–50 (1993)). The binding of other types of molecules with the $PGD_2$ receptor may lead to IOP lowering effects, but with fewer or reduced side effects than the above mentioned $PGD_2$-type analogs.

The relationship of $PGF_{2\alpha}$ receptor activation and IOP lowering effects is not well known. It is believed that $PGF_{2\alpha}$ receptor activation leads to increased outflow of aqueous humor. Regardless of mechanism, $PGF_{2\alpha}$ and analogs have been shown to lower IOP Giuffre, *The Effects of Prostaglandin $F_{2\alpha}$ the Human Eye, Graefe's Archive Ophthalmology,* volume 222, pages 139–141 (1985); and Kerstetter et al., *Prostaglandin $F_{2\alpha}$-1-Isopropylester Lowers Intraocular Pressure Without Decreasing Aqueous Humor Flow, American Journal of Ophthalmology,* volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology,* volume 229, pages 411–413 (1991)). Though $PGF_{2\alpha}$-type molecules lower IOP, these types of molecules have also been associated with undesirable side effects resulting from topical ophthalmic dosing. Such effects include an initial increase in IOP, breakdown of the blood aqueous barrier and conjunctival hyperemia (Alm, *The Potential of Prostaglandin Derivatives in Glaucoma Therapy*, Current Opinion in Ophthalmology, volume 4, No. 11, pages 44–50 (1993)). The binding of other types of molecules with the $PGF_{2\alpha}$ receptor with other types of molecules may lead to IOP lowering effects, but with less side effects than those elicited by the above mentioned $PGF_{2\alpha}$-type analogs.

Based on the foregoing, a need exists for the development of molecules that will activate the $PGD_2$ and $PGF_{2\alpha}$ receptors, yielding a more efficacious lowering of IOP, while exhibiting fewer or reduced side effects.

SUMMARY OF THE INVENTION

The present invention is directed to compositions and methods of their use in treating IOP and ocular hypertension. In particular, the present invention provides combinations of DP-agonists (hereinafter defined) and FP-agonists (hereinafter defined), and methods of their use in treating glaucoma and ocular hypertension.

The present invention takes advantage of the use of two different prostaglandin-type molecules for lowering IOP. In administering these compounds in a combination composition, the amounts of each compound can be decreased, thus reducing side effects attributable to higher quantities of the individually dosed compounds, while achieving the same or greater effect on lowering IOP.

DETAILED DESCRIPTION OF THE INVENTION

The present invention makes use of a combination of a DP-agonist and a FP-agonist or lowering IOP. While Applicants do not wish to be bound by any theory, the D-prostaglandins ("DP-agonist") are believed to inhibit aqueous humor inflow into the eye, while the F-prostaglandins ("FP-agonist") are believed to increase the outflow of aqueous humor from the eye. Therefore, the use of a combination of a DP-agonist and a FP-agonist may lead to more efficacious lowering of IOP, and a reduced magnitude of side effects.

The DP-agonists of the present invention are useful in lowering IOP in humans and other mammals. The DP-agonists of the present invention are functionally defined by their ability to bind to prostaglandin-$D_2$ receptors of cells and evoke similar responses as when $PGD_2$ binds these receptors, inducing the lowering of IOP. Various assays may be used for the determination of DP-agonists.

Binding assays may be used to elucidate DP-agonists of the present invention. Sharif has described a receptor binding assay in: Sharif, N. A., Williams, G. W. and DeSantis, L. M., *Neurochemistry Research*, volume 20, pages 669–674 (1995), the entire contents of which are incorporated herein by reference, and may be modified as described below, for the elucidation of DP-agonists of the present invention. Briefly, the binding assays are conducted in 25 mM Tris HCl (pH 7.4) containing 138 mM NaCl, 5 mM $MgCl_2$, and 1 mM EDTA. Frozen-thawed expired human blood platelets (40–60 mg/ml stock) are incubated in a total volume of 500 $\mu$l with 2–10 nM [$^3$H]$PGD_2$ in the absence and presence of 100 $\mu$M unlabeled $PGD_2$ to define total and non-specific binding, respectively. The incubations (20 minutes at 23° C.) are terminated by rapid vacuum filtration, using a Whatman GF/B glass fiber filter previously soaked in 1% polyethyleneimine and 0.1% BSA, and the receptor-bound radioactivity is then determined by scintillation spectrometry. The binding data are analyzed using a non-linear, iterative curve-fitting computer program to define the receptor binding affinity ($K_i$) of the compounds. Compounds which exhibit $K_i$ values in this assay of less than or equal to about 20 $\mu$M are within the definition of DP-agonists of the present invention.

The DP-agonists of the present invention may also be defined functionally, by their ability to stimulate adenylate cyclase activity. Sharif has described this type of functional assay in: Sharif, N. A., Xu, S. and Yanni, J. M., *Journal of Ocular Pharmacology*, volume 10, pages 653–664 (1994), the entire contents of which are incorporated herein by reference, and which may be modified as described below, for the elucidation of DP-agonists of the present invention. Briefly, functional adenylate cyclase activity is determined using embryonic bovine tracheal cells (EbTr) cells. Cultured cells are stimulated with the test compound for 15 minutes at 23° C. The reaction is then stopped and the cAMP generated is determined by a radioimmunoassay kit. Data are analyzed using a non-linear, iterative curve-fitting computer program to define the potency ("$EC_{50}$", concentration which produces 50% of the maximum response of $PGD_2$) and efficacy of the compounds. Compounds which exhibit $EC_{50}$ values of less than or equal to about 10 $\mu$M are within the DP-agonist definition of the present invention.

It has unexpectedly been found that 3-Oxa-D-prostaglandins ("3-O-DP") are more efficacious in lowering and controlling IOP than their 3-carba analogs. Consequently, these 3-O-DPs can be administered at lower doses than their 3-carba analogs. The lower doses are believed to reduce their activity on other prostaglandin receptors and thereby reduce many of the aforementioned undesirable side effects.

Preferred DP-agonists of the present invention are of the following formula (III):

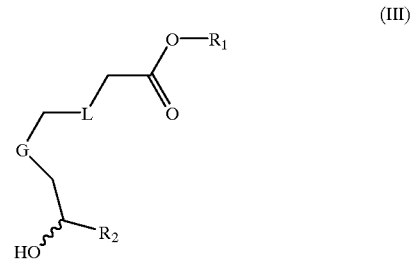

(III)

wherein:

$R_1$ is H, alkyl or alkylcyloalkyl;

$R_2$ is alkyl, cycloalkyl or alkylcycloalkyl;

L is carbon or oxygen; and

G is

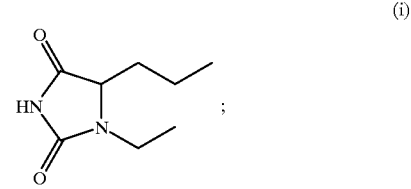

(i)

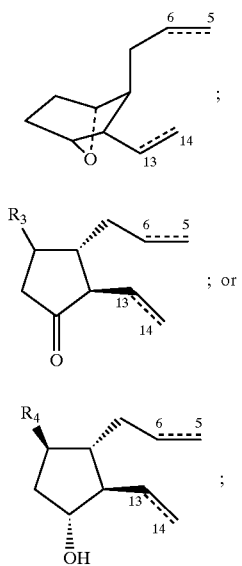

wherein:
R₃ is H, OH or alkyl;
R₄ is H, F, Cl, I, or $C_{1-3}$ alkyl;
——— represents a single bond or double bond; provided that when a double bond is between the 13 and 14 position it is in the trans configuration; when L is carbon, G may also be

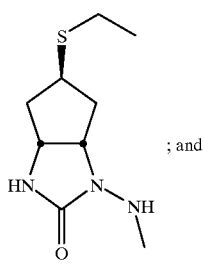

pharmaceutically acceptable salts thereof.

More preferably, the DP-agonists of the present invention are those of formula (III), wherein one or more of the following substituents is selected:
G is (ii) or (iv);
R₄ is Cl;
R₂ is cyclohexyl;
L is oxygen;
R₁ is isopropyl; and
the bond between the 5 and 6 position is a cis configured double bond.

The most preferred DP-agonist of the present invention is of formula (III) wherein: G is (iv); R₄ is Cl; R₂ is cyclohexyl; L is oxygen; R₄ is isopropyl; the bond between position 13 and 14 is saturated; and the bond between the 5 and 6 position is a cis configured double bond. Some of the DP-agonists of the present invention are believed to be novel.

The DP-agonists of the present invention, aside from those compounds which are believed to be novel, are known to those skilled in the art, and some are available commercially or may be made by methods known to those skilled in the art. Novel compounds of the present invention may be prepared by analogous synthetic routes as those which are known.

The DP-agonists wherein G is formula (i), are described in Barraclough, *Synthesis and Platelet Aggregation Inhibiting Activity of Acid Side-chain Modified Hydantoin Prostaglandin Analogues, Archives in Pharmacology,* volume 326, No. 2, pages 85–95 (1993), the entire contents of which are incorporated herein by reference.

The DP-agonists wherein G is formula (ii), may be prepared from [1S-[1α, 2α(Z), 3α(1E, 3S), 4α]]-7-[3-(3-Cyclohexyl-3-hydroxy-1-propenyl)-7-oxabicyclo[2.2.1]hept-2-yl]-5-heptenoic acid following the procedure described in Das, *9,11-Epoxy-9-homoprosta-5-enoic Acid Analogues as Thromboxane A₂Receptor Antagonists, Journal of Medicinal Chemistry,* volume 33, No. 6, pages 1741–1748 (1990), for the conversion of [1S-[1α, 2α(Z), 3α(1E, 3S, 4R)), 4α]]-7-[3-[4-phenyl-3-(tetrahydropyran-2-yloxy)-1-pentyl]-7-oxabicyclo[2.2.1]hept-2-yl]-5-heptenoic acid to [1S-[1α, 2α(Z), 3α(1E, 3S, 4R)), 4α]]-[[4-[3(3-hydroxy-4-phenyl-1-pentyl)-7-oxabicyclo[2.2.1]hept-2-yl]-5-heptenoic acid.

The DP-agonists wherein G is formula (iii), may be prepared from (5Z, 13E)-9S, 11R, 15S)-15 cyclohexyl-9-hydroxy-3-oxa-11,15-bis(tetrahyropyran-2-yloxy)-16, 17, 18, 19, 20-pentanor-5,13-prostanoic acid tert butyl ester (EP 299 914) by the method described in Bundy, *Synthesis and Platelet Aggregation Inhibiting Activity of Prostaglandin D Analogues, Journal of Medicinal Chemistry,* volume 26, pages 790–799 (1983), the entire contents of which are incorporated herein by reference.

The DP-agonists wherein G is formula (iv) are disclosed in WIPO Publication NO. WO 94/05631, and is incorporated herein by reference to the extent this publication teaches the synthesis of the compounds contained therein.

The DPs of the present invention wherein G is (v) are disclosed in European Patent Application Publication No. 0 458 642 A1, and is incorporated herein by reference to the extent this publication teaches the synthesis of the compounds contained therein.

The FP-agonists of the present invention are useful in lowering IOP in humans and other mammals. The FP-agonists of the present invention are of the following formula (IV):

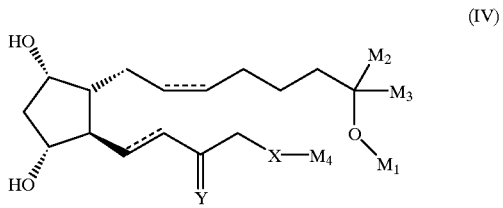

wherein:
X is CH₂or O;
Y is H and OH or O;
M₁ is H, $C_{1-12}$ straight-chain or branched alkyl; $C_{1-12}$ straight chain or branched
acyl; $C_{3-8}$ cycloalkyl; a cationic salt moiety; or an acceptable amine moiety;
M₂ and M₃ are H or taken together are (=O); and $M_4$ is $C_{3-5}$ alkyl or

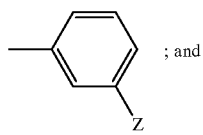 ; and

Z is H, Cl or $CF_3$;

provided that when $M_2$ and $M_3$ taken together are (=O), then $M_1$ cannot be $C_{1-12}$ straight chain or branched acyl; and when $M_2$ and $M_3$ are H, then $M_1$ cannot be a salt or an amine.

The following are preferred FP-agonists of formula (IV): the esters latanoprost and UFO-21, as well as, cloprostenol, fluprostenol, 13,14 dihydro-cloprostenol and 13,14-dihydrofluprostenol and their isopropyl esters and salts.

The most preferred FP-agonist of the present invention is latanoprost.

The FP-agonists of the present invention are known and are commercially available, or may be prepared by known methods to those skilled in the art. Some of the FP-agonists of the present invention are disclosed in European Patent Publication No. 0 639 563 A2, which is incorporated herein by reference to the extent that it discloses methods of synthesizing or obtaining FP-agonists of the present invention.

The combinations of a DP-agonist and a FP-agonist of the present invention are useful in lowering intraocular pressure and thus are useful in the treatment of glaucoma. As compared with therapeutically effective dosages of the individual components, the combinations produce significantly fewer unwanted side effects such as marked vasoconstriction or vasodilation of the vessels of the sclera, painful stinging and intraocular inflammation.

The DP-agonists and FP-agonists of the present invention may be formulated either separately or in the same pharmaceutical compositions. Thus, the DP-agonists and FP-agonists of the present invention can be administered simultaneously or sequentially to humans and other mammals as a treatment of glaucoma or ocular hypertension. When formulated separately the DP-agonists and FP-agonists of the present invention may be administered 1) concomitantly; 2) within a short delay between one agent and the other; 3) in an offset manner, such as the DP-agonist in the morning and the FP-agonist in the evening, or in reverse order; and 4) such that the DP-agonist is dosed both in the morning and evening and FP-agonist is dosed in the evening. It is preferred that the DP-agonist be dosed first and shortly thereafter (i.e., 5–30 minutes) the FP-agonist be dosed.

The DP-agonists and FP-agonists of the present invention are useful in lowering intraocular pressure and thus are useful in the treatment of glaucoma. The preferred route of administration is topical. As used herein, the term "pharmaceutically effective amount" refers to that amount of a DP-agonist and FP-agonist formulated separately, or a combination of a DP-agonist and FP-agonist formulated together, which lowers IOP when administered to a mammal. The compounds of the present invention can be administered as solutions, suspensions, or emulsions (dispersions) in a suitable ophthalmic vehicle.

In forming compositions for topical administration, the compounds of the present invention are generally formulated as between about 0.00005 to about 0.5 percent by weight (wt %) solutions in water at a pH between 4.5 to 7.4.

The compounds are preferably formulated between about 0.0003 to about 0.3 wt % and, most preferably, between about 0.0005 and about 0.03 wt %. While the precise regimen is left to the discretion of the clinician, it is recommended that the resulting solution or solutions be topically applied by placing one drop of each solution(s) in each eye one or two times a day.

Other ingredients which may be desirable to use in the ophthalmic preparations of the present invention include preservatives, co-solvents and viscosity building agents.

Preferred formulations of DP-agonists and FP-agonists combinations of the present invention include the following Examples 1–3:

EXAMPLE 1

| Ingredient | Amount (wt %) |
| --- | --- |
| DP-agonist | 0.001 |
| FP-agonist | 0.001 |
| Phosphate Buffered Saline | 1.0 |
| Benzalkonium Chloride | 0.01 |
| Polysorbate 80 | 0.5 |
| Purified water | q.s. to 100% |

EXAMPLE 2

An example of two formulations to be used concomitantly, within 30 minutes, or offset by more than 1 hour.

Formulation A

| Ingredient | Amount (wt %) |
| --- | --- |
| DP-agonist | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

Formulation B

| Ingredient | Amount (wt %) |
| --- | --- |
| FP-agonist | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 3

| Ingredient | Amount (wt %) |
| --- | --- |
| DP-agonist | 0.0005 |
| FP-agonist | 0.0005 |
| Phosphate Buffered Saline | 1.0 |
| Hydroxypropyl-β-cyclodextrin | 4.0 |
| Purified water | q.s. to 100% |

What is claimed is:

1. A method of treating glaucoma or ocular hypertension in mammals which comprises administering to the mammal a pharmaceutically effective amount of the combination of:

(a) a non-hyperemic amount of one or more DP-agonists of formula (III):

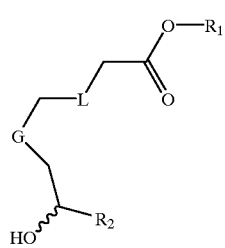

(III)

wherein:

$R_1$ is H, alkyl or alkylcyloalkyl;

$R_2$ is alkyl, cycloalkyl or alkylcycloalkyl;

L is carbon or oxygen; and

G is

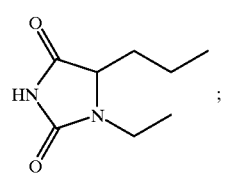

(i)

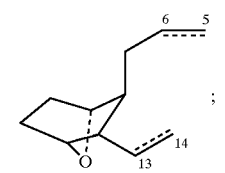

(ii)

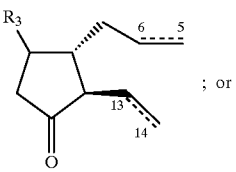

(iii); or

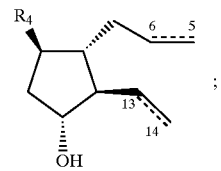

(iv)

wherein:

$R_3$ is H, OH or alkyl;

$R_4$ is H, F, Cl, I, or $C_{1-3}$ alkyl;

— — — — represents a single bond or double bond; provided that when a double bond is between the 13 and 14 position it is in the trans configuration;

when L is carbon, G may also be

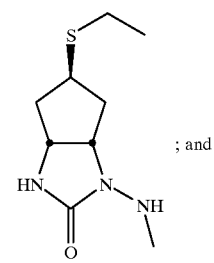

(v)

; and and pharmaceutically acceptable salts thereof, and (b) a non-inflammatory amount of one or more FP-agonists of formula (IV):

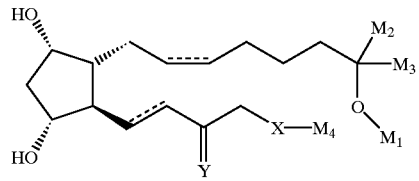

(IV)

wherein:

X is $CH_2$ or O;

Y is H and OH or O;

$M_1$ is H, $C_{1-12}$ straight-chain or branched alkyl; $C_{1-12}$ straight chain or branched acyl; $C_{3-8}$ cycloalkyl; a cationic salt moiety; or an acceptable amine moiety;

$M_2$ and $M_3$ are H or taken together are (=O); and $M_4$ is $C_{3-5}$ alkyl or

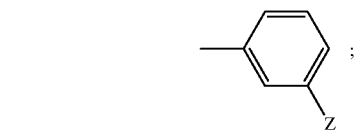

;

Z is H, Cl or $CF_3$; and provided that when $M_2$ and $M_3$ taken together are (=O), then $M_1$ cannot be $C_{1-12}$ straight chain or branched acyl; and when $M_2$ and $M_3$ are H, then $M_1$ cannot be a salt or an amine; wherein the DP and FP-agonists are administered concomitantly or within 30 minutes of each other, and wherein the amounts of the DP and FP-agonists, separately, are not effective in treating glaucoma or ocular hypertension.

2. The method of claim 1 wherein the DP agonist is selected from the group consisting of molecules containing one or more of the following substituents:

G is (iv); $R_4$ is Cl; $R_2$ is cyclohexyl; L is oxygen; $R_1$ is isopropyl; the bond between position 13 and 14 is saturated; and the bond between the 5 and 6 position is a cis configured double bond.

3. The method of claim 1 wherein the FP-agonist is selected from the group consisting of molecules containing one or more of the following substituents:

$M_1$ is H or isopropyl; $M_2$ and $M_3$ taken together are (=O); $M_4$ is

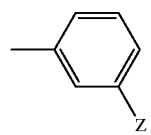

or $C_5$ alkyl; and

Z is H, Cl or $CF_3$.

4. The method of claim 2 wherein the DP-agonist has the formula wherein G is (iv); $R_4$ is Cl; $R_2$ is cyclohexyl; L is oxygen; $R_1$ is isopropyl; the bond between position 13 and 14 is saturated; and the bond between the 5 and 6 position is a cis configured double bond.

5. The method of claim 3 wherein the FP-agonist is selected from the group consisting of: latanoprost and UFO-21; and cloprostenol, fluprostenol, 13,14 dihydro-cloprostenol, 13,14-dihydrofluprostenol and their isopropyl esters and salts thereof.

6. The method of claim 1 wherein, (a) the DP-agonist is selected from the group consisting of molecules containing one or more of the following substituents: G is (iv); $R_4$ is Cl; $R_2$ is cyclohexyl; L is oxygen; $R_1$ is isopropyl; the bond between position 13 and 14 is saturated; and the bond between the 5 and 6 position is a cis configured double bond; and (b) the FP-agonist is selected from the group consisting of molecules containing one or more of the following substituents:

$M_1$ is H or isopropyl; $M_2$ and $M_3$ taken together are (=O); $M_4$ is

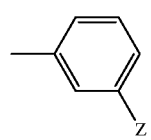

or $C_5$ alkyl; and

Z is H, Cl or $CF_3$.

7. The method of claim 6 wherein:

(a) the DP-agonist has the formula wherein G is (iv); $R_4$ is Cl; $R_2$ is cyclohexyl; L is oxygen; $R_1$ is isopropyl; the bond between position 13 and 14 is saturated; and the bond between the 5 and 6 position is a cis configured double bond; and (b) the FP-agonist is selected from the group consisting of: latanoprost and UFO-21; and cloprostenol, fluprostenol, 13,14 dihydro-cloprostenol, 13,14-dihydrofluprostenol and their isopropyl esters and salts thereof.

8. The method of claim 1 wherein the DP-agonist and FP-agonist are contained in one pharmaceutical composition.

9. The method of claim 1 further comprising administering the DP-agonist and FP-agonist concomitantly, within about 5 to 30 minutes from each other or greater than 2 hours from each other.

10. A composition for treating glaucoma or ocular hypertension in mammals comprising a pharmaceutically acceptable carrier and a pharmaceutically effective amount of a combination of:

(a) a non-hyperemic amount of one or more DP-agonists of formula (III):

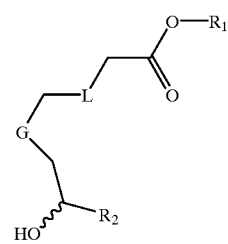

(III)

wherein:

$R_1$ is H, alkyl or alkylcyloalkyl;

$R_2$ is alkyl, cycloalkyl or alkylcycloalkyl;

L is carbon or oxygen; and

G is

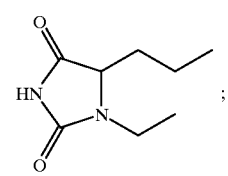

(i)

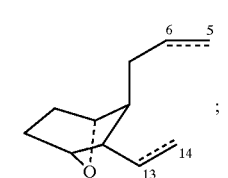

(ii)

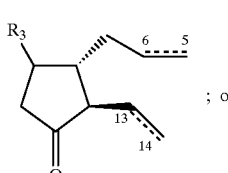

(iii)

; or

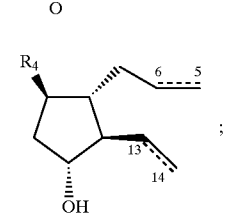

(iv)

wherein:

$R_3$ is H, OH or alkyl;

$R_4$ is H, F, Cl, I, or $C_{1-3}$ alkyl;

— — — — represents a single bond or double bond; provided that when a double bond is between the 13 and 14 position it is in the trans configuration;

when L is carbon, G may also be

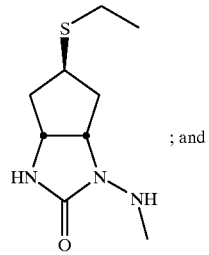

; and and pharmaceutically acceptable salts thereof; and (b) a non-inflammatory amount of one or more FP-agonists of formula (IV):

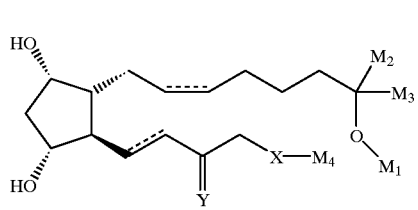

(IV)

wherein:

X is CH$_2$ or O;

Y is H and OH or O;

M$_1$ is H, C$_{1-12}$ straight-chain or branched alkyl; C$_{1-12}$ straight chain or branched acyl; C$_{3-8}$ cycloalkyl; a cationic salt moiety; or an acceptable amine moiety;

M$_2$ and M$_3$ are H or taken together are (=O); and

M$_4$ is C$_{3-5}$ alkyl or

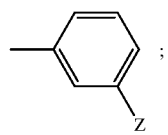

;

Z is H, Cl or CF$_3$; and provided that when M$_2$ and M$_3$ taken together are (=O), then M$_1$ cannot be C$_{1-12}$ straight chain or branched acyl; and when M$_2$ and M$_3$ are H, then M$_1$ cannot be a salt or an amine; wherein the amounts of DP and FP-agonists, separately, are not effective in treating glaucoma or ocular hypertension.

11. The composition of claim 10 wherein the DP agonist is selected from the group consisting of molecules containing one or more of the following substituents:

G is (iv); R$_4$ is Cl; R$_2$ is cyclohexyl; L is oxygen; R$_1$ is isopropyl; the bond between position 13 and 14 is saturated; and the bond between the 5 and 6 position is a cis configured double bond.

12. The composition of claim 10 wherein the FP-agonist is selected from the group consisting of molecules containing one or more of the following substituents:

M$_1$ is H or isopropyl; M$_2$ and M$_3$ taken together are (=O); M$_4$ is

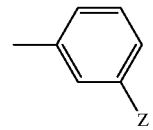

or C$_5$ alkyl; and

Z is H Cl, or CF$_3$.

13. The composition of claim 11 wherein the DP-agonist has the formula wherein G is (iv); R$_4$ is Cl; R$_2$ is cyclohexyl; L is oxygen; R$_1$ is isopropyl; the bond between position 13 and 14 is saturated; and the bond between the 5 and 6 position is a cis configured double bond.

14. The composition of claim 12 wherein the FP-agonist is selected from the group consisting of: latanoprost and UFO-21; and cloprostenol, fluprostenol, 13,14 dihydro-cloprostenol, 13, 14-dihydrofluprostenol and their isopropyl esters and salts thereof.

15. The composition of claim 10 wherein:

(a) the DP agonist is selected from the group consisting of molecules containing one or more of the following substituents: G is (iv); R$_4$ is Cl; R$_2$ is cyclohexyl; L is oxygen; R$_1$ is isopropyl; the bond between position 13 and 14 is saturated; and the bond between the 5 and 6 position is a cis configured double bond; and (b) the FP-agonist is selected from the group consisting of molecules containing one or more of the following substituents:

M$_1$ is H or isopropyl; M$_2$ and M$_3$ taken together are (=O); M$_4$ is

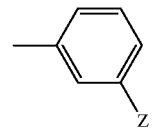

or C$_5$ alkyl; and

Z is H, Cl or CF$_3$.

16. The composition of claim 15 wherein:

(a) the DP-agonist has the formula wherein G is (iv); R$_4$ is Cl; R$_2$ is cyclohexyl; L is oxygen; R$_1$ is isopropyl; the bond between position 13 and 14 is saturated; and the bond between the 5 and 6 position is a cis configured double bond; and (b) The FP-agonist is selected from the group consisting of: latanoprost and UFO-21; and cloprostenol, fluprostenol, 13,14 dihydro-cloprostenol, 13,14-dihydrofluprostenol and their isopropyl esters and salts thereof.

* * * * *